United States Patent [19]

Nakao et al.

[11] Patent Number: 5,264,191

[45] Date of Patent: * Nov. 23, 1993

[54] QUATERNARY AMMONIUM TRIHALIDE AND METHOD FOR DISSOLUTION OF METAL WITH LIQUID CONTAINING THE COMPOUND

[75] Inventors: Yukimichi Nakao, Tsukuba; Kyoji Kaeriyama, Tsuchiura, both of Japan

[73] Assignees: Agency of Industrial Science and Technology; Ministry of International Trade and Industry, Tokyo, Japan

[*] Notice: The portion of the term of this patent subsequent to Aug. 18, 2009 has been disclaimed.

[21] Appl. No.: 888,380

[22] Filed: May 22, 1992

Related U.S. Application Data

[62] Division of Ser. No. 739,235, Aug. 1, 1991, abandoned.

[30] Foreign Application Priority Data

Aug. 28, 1990 [JP] Japan .................................. 2-226297

[51] Int. Cl.$^5$ ........................... C01B 9/00; C01G 1/06; C01G 7/00; C01G 5/00
[52] U.S. Cl. ........................................ 423/22; 423/27; 423/32; 423/51; 423/56; 423/87; 423/98; 423/38; 423/109; 423/150.1; 423/658.5
[58] Field of Search ................. 423/22, 27, 32, 51, 423/56, 87, 98, 38, 109, 150.1, 658.5; 75/722

[56] References Cited

U.S. PATENT DOCUMENTS

| | | | |
|---|---|---|---|
| 3,279,981 | 10/1966 | Geiger et al. | 514/642 |
| 5,120,523 | 6/1992 | Nakao et al. | 423/491 |
| 5,139,752 | 8/1992 | Nakao et al. | 423/658.5 |

FOREIGN PATENT DOCUMENTS 14411 2/1974 Japan .

OTHER PUBLICATIONS

Cotton, A. F. et al, Advanced Inorganic Chemistry, 1966, p. 589.

*Primary Examiner*—Michael Lewis
*Assistant Examiner*—Steven Bos
*Attorney, Agent, or Firm*—Oblon, Spivak, McClelland, Maier & Neustadt

[57] ABSTRACT

A quaternary ammonium trihalide, a novel compound, represented by the formula:

$$[A-R']^+ X_3^-$$

(wherein A stands for a trialkyl-amino radical or a pyridyl radical, R' for an alkyl radical of 6 to 22 carbon atoms, and X for a halogen atom) and a method for the dissolution of a metal with a liquid consisting essentially of an organic solvent and the quaternary ammonium trihalide.

6 Claims, No Drawings

QUATERNARY AMMONIUM TRIHALIDE AND METHOD FOR DISSOLUTION OF METAL WITH LIQUID CONTAINING THE COMPOUND

This application is a division of application Ser. No. 07/739,235, filed on Aug. 1, 1991, now abandoned.

BACKGROUND OF THE INVENTION

1. Field of the Invention

This invention relates to novel quaternary ammonium trihalides soluble in organic solvent and a method for the dissolution of metal which is useful for the extraction and recovery of the metal.

2. Description of the Prior Art

The dissolution of a metal is an indispensable step in the extraction and recovery of the metal from a mixture in which it is contained and, as such, is highly important from the industrial point of view. The conventional method used for this dissolution has been to dissolve the metal in an aqueous solution of an inorganic acid such as hydrochloric acid.

The conventional method of dissolution by use of an inorganic acid is dangerous to conduct because of the need to use a strongly acidic aqueous solution. Moreover, it generates a large volume of waste water that requires expensive processing for disposal.

With a view to overcoming such drawbacks of the prior art described above, the present inventors earlier conducted various studies in search of a method for effecting the dissolution of metals without use of any inorganic acid and consequently developed a method for the dissolution of metals by contacting the metal with a halogenated hydrocarbon in the presence of a surfactant. They were granted U.S. Pat. No. 4,919,716 on this invention.

This method, however, has a problem in that since the surfactant has a large molecular weight, the consumption thereof necessary for the dissolution amounts to a large number of grams.

Through further studies the inventors learned that many metals are dissolved when they are brought into contact with a quarternary ammonium compound and a halogenated hydrocarbon optionally, further with a polar solvent. This invention was filed for paten under U.S. Application Ser. No. 07/603,438 dated Oct. 26, 1990, now U.S. Pat. No. 5,120,523.

Though this method provides highly satisfactory dissolution for various metals, it still falls short of satisfying the practical need for the dissolution to be effected quickly with high efficiency. All of the methods mentioned so far exhibit poor efficiency in the dissolution of gold.

In view of the problems of the earlier methods, the inventors conducted a study for the purpose of developing a method for the dissolution of metal which is capable of easily dissolving metals including gold under moderate conditions as compared with the conventional methods described above. As a result, they learned that novel quaternary ammonium trihalides are produced by the reaction of a cationic surfactant with an elemental halogen and that numerous metals are easily dissolved by contact with an organic solvent in the presence of these quarternary ammonium trihalides. The present invention has been completed as a result.

SUMMARY OF THE INVENTION

The present invetnion is directed to a quaternary ammonium trihalide represented by the general formula:

$$[A-R']^+ \cdot X_3^- \qquad (I)$$

(wherein A stands for one member selected from the group consisting of trialkyl-amino radicals and pyridyl radicals, R' for an alkyl radical of 6 to 22 carbon atoms, and X for a halogen atom) and to a method for the dissolution of a metal which comprises bringing the metal into contact with a liquid consisting essentially of the quaternary ammonium trihalide and an organic solvent.

DESCRIPTION OF THE PREFERRED EMBODIMENTS

The preferable number of carbon atoms in the alkyl radical of the trialkyl-amino group in the quaternary ammonium trihalide is 1 or 2. A trimethylamino group and a triethyl-amino group are concrete examples. As concrete examples of the halogen atom represented by X, bromine and iodine may be cited.

The quaternary ammonium trihalides represented by the formula (I) are novel compounds which have never been reported in the literature.

As quaternary ammonium trihalides producible by the method of this invention, cetylpyridinium tribromide, octyltrimethylammonium tribromide, dodecyltrimethylammonium tribromide, cetyltrimethylammonium tribromide, and cetylpyridinium triiodide, may be cited for example. These compounds have been identified by chemical analysis, X ray analysis and other conventional means.

The method for producing the novel compounds of this invention will now be described.

A cationic surfactant represented by the formula:

$$[A-R']^+ \cdot X^- \qquad (II)$$

(wherein A stands for a trialkyl-amino group or a pyridyl group, R' for an alkyl group of 6 to 22 carbon atoms, and X for a halogen atom) and an elemental halogen are dissolved in a liquid hydrocarbon and caused to react by heating. The resultant quaternary ammonium trihalide is recovered from the reaction mixture by cooling the reaction mixture and filtering the cooled reaction mixture or by evaporating the reaction mixture to dryness to expel the solvent.

The cationic surfactants effectively usable as a raw material herein include hexyltrimethylammonium bromide, dodecyltrimethylammonium bromide, and cetylpyridinium iodide, for example.

The elemental halogens effectively usable as a raw material herein are bromine and iodine.

The hydrocarbons effectively usable as a reaction medium herein include benzene and cyclohexane, for example.

In said reaction method, though the cationic surfactant and the elemental halogen react in an equimolar ratio, the reaction product is generally obtained in a higher yield when the elemental halogen is used in a slight excess. Though the reaction product obtained in this case may possibly contain the excess elemental halogen, this halogen can be easily expelled from the product by leaving it to stand for a long time.

The method for dissolving a metal by the contact of this metal with the quaternary ammonium trihalide of this invention and an organic solvent will now be described in detail.

In the method of this invention, the contact first produces a metal halide by the quaternary ammonium trihalide giving a halogen atom to the metal. As a result, the quaternary ammonium trihalide is reverted to the cationic surfactant, one of the starting raw materials. Then, the metal halide and the cationic surfactant are converted by interreaction into an ion pair of a polyhalogenometal anion complex and a quaternary ammonium cation. This ion pair dissolves in an organic solvent because the quaternary ammonium cation moiety thereof contains a long-chain alkyl group. Depending on the kind of the metal, the possibility arises that the cationic surfactant produced by the first stage reaction, when used alone, will not be sufficient for the reaction of the second stage for the formation of the ion pair. When this possibility is foreseen, it is desirable that the cationic surfactant should be added at first in an excess amount relative to the quaternary ammonium trihalide.

The time required for the dissolution of a metal varies with the metal to be dissolved, the kind and concentration of the quaternary ammonium trihalide, the kind of the organic solvent, and the like. The temperature of the treatment is selected in a range whose upper limit does not exceed the boiling point of the organic solvent to be used. The rate of metal dissolution increases with increasing temperature of the treatment. The end point of the dissolution of the metal can be confirmed by the disappearance of the metal placed in the liquid.

The organic solvents effectively usable herein include liquid hydrocarbons, alcohols, esters, ethers, nitriles, nitrated hydrocarbons, and halogenated hydrocarbons, for example. Benzene, toluene, methanol, ethyl acetate, dioxane, acetonitrile, nitrobenzene, and bromobenzene are concrete examples.

The quantitative relation of the metal to be dissolved to the quaternary ammonium trihalide and the organic solvent is variable with the kinds of the substances involved in the dissolution. Practically, the amount of the organic solvent is approximately in the range of from 3 to 10 g and that of the quaternary ammonium trihalide in the range of from 0.2 to 1.0 mmol per 0.1 mg-atom of the metal.

The metals effectively dissolvable by the method of the present invention include both typical metals and transition metals such as, for example, manganese, iron, cobalt, nickel, copper, zinc, germanium, selenium, palladium, silver, indium, antimony, gold, mercury, and lead. Particularly noteworthy is that gold is dissolved in high efficiency by the method of the present invention, especially as compared with the methods of dissolution described above.

The quaternary ammonium trihalide according with the present invention is a stable compound which is synthesized from inexpensive materials. The metal is dissolved in a mixed liquid consisting of an organic solvent and the quaternary ammonium trihalide. As shown in the working examples cited hereinbelow, the method of this invention for the dissolution of a metal has the advantage that the procedure involved is simple, the organic solvent to be used is an ordinary substance, the method itself is effectively applicable to numerous metals, and it allows easy dissolution of gold as compared with the conventional methods.

EXAMPLES 1 TO 4

In 300 g of benzene, 60 mmols of cetylpyridinium bromide and 66 mmols of bromine were refluxed at a liquid temperature of 80° C. for one hour. The resultant mixture and 300 g of cyclohexane added thereto were cooled to 6° C. in a refrigerator. The crystals which were consequently precipitated in the mixture were separated by filtration and left standing for three days to expel the residual bromine. As a result, there were obtained 27.35 g of yellowish orange crystals of quaternary ammonium trihalide of the following structural formula. This product will be referred to as cetylpyridinium tribromide.

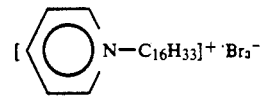

The results of elemental analysis of this compound were as follows.

| As $C_{12}H_{38}NBr_3$ | C | H | N | Br |
| --- | --- | --- | --- | --- |
| Theoretical (%) | 46.34 | 7.04 | 2.57 | 44.05 |
| Found (%) | 46.49 | 7.13 | 2.31 | 43.74 |

In 10 g of each organic solvent indicated in Table 1, 0.5 mmol of cetylpyridinium tribromide and 0.2 mg-atom of a gold wire 0.2 mm in diameter were refluxed under the corresponding conditions indicated in Table 1. In all of the examples, the gold wire was thoroughly dissolved with evolution of a darkish red solution.

TABLE 1

| | | Refluxing | |
| --- | --- | --- | --- |
| Example | Organic solvent | Temperature (°C.) | Time (hr) |
| 1 | Benzene | 80 | 1 |
| 2 | Acetonitrile | 80 | 3 |
| 3 | Ethyl acetate | 77 | 0.5 |
| 4 | Dioxane | 101 | 1 |

EXAMPLES 5 AND 6

In 10 g of benzene, 0.5 mmol of cetylpyridinium tribromide and 0.2 mg-atom of each metal powder indicated in Table 2 were refluxed at 80° C. for the corresponding time indicated in Table 2. In both examples, the metal powder was thoroughly dissolved.

TABLE 2

| Example | Metal powder | Refluxing time (hr) |
| --- | --- | --- |
| 5 | Palladium powder | 0.2 |
| 6 | Cobalt powder | 4 |

EXAMPLES 7 TO 11

In 10 g of benzene, 0.5 mmol of cetylpyridinium tribromide and 0.5 mmol of cetylpyridinium bromide and 0.2 mg-atom of a 0.2 mm wire of each metal indicated in Table 3 were refluxed at 80° C. for the corresponding period indicated in Table 3. In all of the examples, the metal wire was completely dissolved.

TABLE 3

| Example | Metal | Refluxing time (hr) |
| --- | --- | --- |
| 7 | Iron | 1.5 |

TABLE 3-continued

| Example | Metal | Refluxing time (hr) |
| --- | --- | --- |
| 8 | Nickel | 2 |
| 9 | Copper | 1 |
| 10 | Zinc | 1.5 |
| 11 | Silver | 0.5 |

EXAMPLE 12

In 100 g of benzene, 20 mmols of octyltrimethylammonium bromide and 22 mmols of bromine were refluxed at a liquid temperature of 80° C. for one hour. The resultant mixture and 200 g of cyclohexane added thereto were cooled to 6° C. in a refrigerator. The crystals which were consequently precipitated were separated by filtration and left standing for three days to expel the residual bromine. As a result, there were obtained 8.03 g of yellowish orange crystals of quaternary ammonium trihalide of the following structural formula. This compound will be referred to as octyltrimethylammonium tribromide.

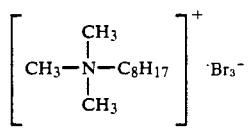

The results of elemental analysis of this compound were as follows.

| As $C_{11}H_{26}NBr_3$ | C | H | N | Br |
| --- | --- | --- | --- | --- |
| Theoretical (%) | 32.06 | 6.36 | 3.40 | 58.18 |
| Found (%) | 32.79 | 6.47 | 3.32 | 57.99 |

In 10 g of benzene, 0.5 mmol of octyltrimethylammonium tribromide, 0.5 mmol of octyltrimethylammonium bromide, and 0.2 mg-atom of a 0.2 mm gold wire were refluxed at a liquid temperature of 80° C. for 1.5 hours. In all of the examples, the gold wire was completely dissolved with evolution a darkish red solution.

EXAMPLE 13

In 100 g of benzene, 20 mmols of dodecyltrimethylammonium bromide and 22 mmols of bromine were refluxed at a liquid temperature of 80° C. for one hour. The resultant mixture and 100 g of cyclohexane added thereto were cooled to 6° C. in a refrigerator. The crystals which were consequently precipitated were separated by filtration and left standing for three hours to expel the residual bromine. As a result, there were obtained 9.28 g of yellowish orange crystals of quaternary ammonium trihalide of the following structural formula. This compound will be referred to as dodecyltrimethylammonium tribromide.

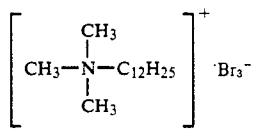

The results of elemental analysis of this compound were as follows.

| As $C_{15}H_{34}NBr_3$ | C | H | N | Br |
| --- | --- | --- | --- | --- |
| Theoretical (%) | 38.48 | 7.32 | 2.99 | 51.21 |
| Found (%) | 38.65 | 7.38 | 2.94 | 50.51 |

In 10 g of benzene, 0.5 mmol of dodecyltrimethylammonium tribromide, 0.5 mmol of dodecyltrimethylammonium bromide, and 0.2 mg-atom of a 0.2 mm gold wire were refluxed at a liquid temperature of 80° C. for one hour. The gold wire was completely dissolved with evolution of a darkish red solution.

EXAMPLE 14

In 100 g of benzene, 20 mmols of cetyltrimethylammonium bromide and 22 mmols of bromine were refluxed at a liquid temperature of 80° C. for one hour. The resultant mixture and 100 g of cyclohexane added thereto were cooled to 6° C. in a refrigerator. The crystals which were consequently precipitated were separated by filtration and left standing for three days to expel the residual bromine. As a result, there were obtained 9.28 g of yellowish orange crystals of quaternary ammonium trihalide of the following structural formula. This compound will be referred to as cetyltrimethylammonium tribromide.

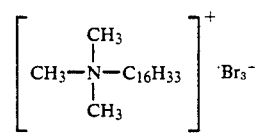

The results of elemental analysis of this compound were as follows.

| As $C_{19}H_{42}NBr_3$ | C | H | N | Br |
| --- | --- | --- | --- | --- |
| Theoretical (%) | 43.53 | 8.08 | 2.67 | 45.73 |
| Found (%) | 43.64 | 8.07 | 2.38 | 45.25 |

In 10 g of benzene, 0.5 mmol of cetyltrimethylammonium tribromide, 0.5 mmol of cetyltrimethylammonium bromide, and 0.2 mg-atom of a gold wire 0.2 mm in diameter were refluxed at a liquid temperature of 80° C. for 1.5 hours. The gold wire was completely dissolved with evolution of a darkish red solution.

EXAMPLE 15

In 100 g of benzene, 10 mmols of cetylpyridinium iodide and 11 mmols of iodine were refluxed at a liquid temperature of 80° C. for one hour. The resultant mixture and 100 g of cyclohexane added thereto were cooled to 6° C. in a refrigerator. The crystals consequently precipitated were separated by filtration. As a result, there were obtained 5.92 g of darkish brown crystals of quaternary ammonium trihalide of the following structural formula. This compound will be referred to as cetylpyridinium triiodide.

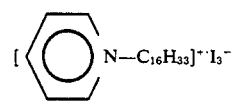

The results of elemental analysis of this compound were as follows.

| As $C_{21}H_{38}NI_3$ | C | H | N | I |
|---|---|---|---|---|
| Theoretical (%) | 36.81 | 5.59 | 2.04 | 55.56 |
| Found (%) | 36.64 | 5.79 | 2.02 | 56.40 |

In 10 g of benzene, 0.5 mmol of cetylpyridinium triiodide, 0.5 mmol of cetylpyridinium iodide, and 0.2 mg-atom of a 0.2 mm gold wire were refluxed at a liquid temperature of 80° C. for 0.5 hour. The gold wire was completely dissolved with evolution of a deep darkish red solution.

What is claimed is:

1. A method for the dissolution of a metal which comprises bringing said metal into contact with a liquid consisting essentially of an organic solvent and a quaternary ammonium trihalide represented by the formula:

$$[A—R']^+ X_3^-$$

wherein A is selected from the group consisting of a trialkylamino radical and a pyridyl radical, R' is an alkyl radical of 6 to 22 carbon atoms, and X is a halogen atom.

2. A method according to claim 1, wherein the number of carbon atoms of each alkyl radical of said trialkyl-amino radical is 1 or 2.

3. A method according to claim 1, wherein the halogen atom in said quaternary ammonium trihalide is one member selected from the group consisting of bromine and iodine.

4. A method according to claim 1, wherein said quaternary ammonium trihalide is one member selected from the group consisting of the compounds represented by the following formulas:

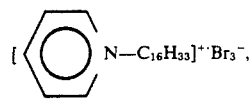

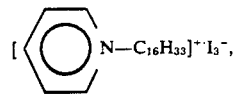

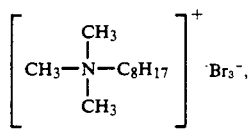

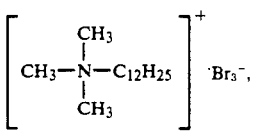

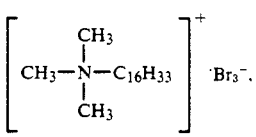

5. A method according to claim 1, wherein said metal is at least one member selected from the group consisting of manganese, iron, cobalt, nickel, copper, zinc, germanium, selenium, palladium, silver, indium, antimony, gold, mercury, and lead.

6. A method according to claim 5, wherein said metal is at least one member selected from the group consisting of gold, iron, nickel, copper, zinc, and silver.

* * * * *